(12) United States Patent
Abensour et al.

(10) Patent No.: US 8,117,020 B2
(45) Date of Patent: Feb. 14, 2012

(54) METHOD TO DETERMINE THE DEGREE AND STABILITY OF BLOOD GLUCOSE CONTROL IN PATIENTS WITH DIABETES MELLITUS VIA CREATION AND CONTINUOUS UPDATING OF NEW STATISTICAL INDICATORS

(75) Inventors: Daniel S. Abensour, Coral Springs, FL (US); R. Mack Harrell, Boca Raton, FL (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 228 days.

(21) Appl. No.: 12/437,933

(22) Filed: May 8, 2009

(65) Prior Publication Data
US 2009/0216460 A1    Aug. 27, 2009

Related U.S. Application Data

(63) Continuation-in-part of application No. 11/293,534, filed on Dec. 3, 2005, now abandoned.

(60) Provisional application No. 60/632,585, filed on Dec. 3, 2004.

(51) Int. Cl.
*G06G 7/58* (2006.01)
*G01N 33/48* (2006.01)
*G01N 31/00* (2006.01)
*C12Q 3/00* (2006.01)

(52) U.S. Cl. ............ 703/11; 703/12; 702/19; 702/22; 435/3

(58) Field of Classification Search .............. None
See application file for complete search history.

(56) References Cited

FOREIGN PATENT DOCUMENTS
WO    2004027676 A2    4/2004

OTHER PUBLICATIONS

Percentage (in Mathematics). Dictionary of Engineering Terms, Butterworth-Heinemann, 2001, one page. Retrieved online on May 13, 2011 from <<http://www.credoreference.com/entry/bhidet/percentage_in_mathematics>>.*
Variance. Hargrave's Communications Dictionary, Wiley, 2001, one page. Retrieved online on May 13, 2011 from <<http://www.credoreference.com/entry/hargravecomms/variance>>.*
Standard error or standard error of the mean. Chambers 21$^{st}$ Century Dictionary, 2001, one page. Retrieved online on May 13, 2011 from <<http://www.credoreference.com/entry/chambdict/standard_error_or_standard_error_of_the_mean>>.*

(Continued)

*Primary Examiner* — Russell S Negin
(74) *Attorney, Agent, or Firm* — Dinsmore & Shohl LLP

(57) ABSTRACT

Systems and methods for determining a stability of a blood glucose concentration of a patient are provided. The system comprises a processor that may be programmed to receive blood glucose concentration test results each taken from the patient at a different time over a time period and to compute a time-averaged glucose parameter indicative of blood glucose concentration control over the time period. In addition, the processor may be programmed to compute a virtual blood hemoglobin parameter through a simulated measurement of a blood hemoglobin, the virtual blood hemoglobin parameter being indicative of blood glucose concentration control over an extended time period encompassing the time period. Further, the processor may be programmed to compute a lability factor parameter indicative of a variability in blood glucose concentration over the time period.

18 Claims, 10 Drawing Sheets

OTHER PUBLICATIONS

Newton-Cotes Rule. Penguin Dictionary of Mathematics, 2008, one page. Retrieved online on May 13, 2011 from <<http://www.credoreference.com/entry/penguinmath/newton_cotes_rule>>.*

Merino-Torres et al. Hemoglobin glycosylation index is not related with blood glucose. Journal of Diabetes and Its Complications, vol. 17, Sep.-Oct. 2003, pp. 249-253.*

Proof of date of [Merino-Torres et al. Hemoglobin glycosylation index is not related with blood glucose. Journal of Diabetes and Its Complications, vol. 17, Sep.-Oct. 2003, pp. 249-253.], one page printed on May 12, 2011.*

Waveform, average value of (in Mathematics). Dictionary of Engineering Terms, Butterworth-Heinemann, 2001, two pages. Retrieved online on Oct. 15, 2011 from <<http://www.credoreference.com/entry/bhidet/waveform_average_value_of_in_mathematics.* de Lissovoy, Gregory et al., "Relationship of Hemoglobin Age of Diabetes Diagnosis, and Ethnicity to Clinical Outcomes and Medical Costs in a Computer-Simulated Cohort of Persons With Type 2 Diabetes", The American Journal of Managed Care, vol. 6., No. 5, May 2000, pp. 573-584.

Le Floch, Jean-Pierre et al., "Blood Glucose Area Under the Curve", Diabetes Care, vol. 13., No. 2, Feb. 1990, pp. 172-175.

* cited by examiner

| Results | 200 | |
|---|---|---|
| Start Date | 9-Aug-05 | |
| End Date | 9-Nov-05 | |
| Glycostator Summary | | |
| Time Averaged Glucose | 144.20 | |
| Corresponding Virtual A1C | 6.90 | Good Control |
| Lability Index | 47% | Acceptable |
| Summary of Test Results | | |
| Number of Tests | 558 | |
| Average number of tests/day: | 6.10 | |
| Hypoglycemic: | 15% | 84 |
| Hyperglycemia: | 38% | 214 |
| In Range: | 47% | 260 |
| Standard Deviation: | 67.10% | |
| Average | 145.22 | |

| Guidelines | 202 |
|---|---|
| TAG Range | 70 – 120 |
| VA1c Control | |
| IDEAL | 4.5 – 6.0 |
| Good Control | 6.1 – 7.0 |
| Fair | 7.1 – 8.0 |
| Suboptimal | 8.1 – 9.0 |
| Poor | >9.0 |
| Lability Index | |
| IDEAL | <30% |
| Acceptable | 30% – 50% |
| Labile | 50% – 70% |
| Extremely Labile | >70% |

FIG. 2

| HbA1c(%) | Average | |
|---|---|---|
| 4 | 50 | |
| 5 | 83 | Non-Diabetic Range |
| 6 | 116 | |
| 7 | 149 | Target for Diabetes in Control |
| 8 | 182 | Action recommended following ADA guidelines |
| 9 | 215 | |
| 10 | 248 | |
| 11 | 281 | |
| 12 | 314 | |

| Test # k | Global Time (minutes) | Result # k | γ k coefficient | Ak* Time Average Glucose | Pk | Running Average | VA1c |
|---|---|---|---|---|---|---|---|
| 1 | 1515 | 232 | 0.97 | 232.00 | 232.00 | 232.00 | 9.52 |
| 2 | 2011 | 167 | 0.97 | 199.50 | 193.52 | 199.50 | 8.35 |
| 3 | 2236 | 225 | 0.97 | 198.41 | 192.46 | 208.00 | 8.32 |
| 4 | 2440 | 170 | 0.97 | 198.21 | 192.26 | 198.50 | 8.31 |
| 5 | 2542 | 171 | 0.97 | 195.46 | 189.59 | 193.00 | 8.23 |
| 6 | 2590 | 142 | 0.97 | 193.72 | 187.90 | 184.50 | 8.18 |
| 7 | 2937 | 191 | 0.98 | 187.07 | 181.70 | 185.43 | 7.99 |
| 8 | 3352 | 165 | 0.98 | 185.02 | 180.06 | 182.88 | 7.94 |
| 9 | 3697 | 145 | 0.98 | 180.28 | 175.60 | 178.67 | 7.81 |
| 10 | 4015 | 93 | 0.98 | 172.48 | 168.10 | 170.10 | 7.58 |
| 11 | 4332 | 90 | 0.99 | 163.37 | 159.33 | 162.82 | 7.31 |
| 12 | 4836 | 187 | 0.99 | 159.60 | 155.96 | 164.83 | 7.21 |
| 13 | 5136 | 108 | 0.99 | 158.59 | 155.13 | 160.46 | 7.19 |
| 14 | 5499 | 87 | 0.99 | 153.03 | 149.79 | 155.21 | 7.02 |
| 15 | 5640 | 61 | 0.99 | 150.33 | 147.18 | 148.93 | 6.94 |
| 16 | 5702 | 92 | 0.99 | 149.23 | 146.12 | 145.38 | 6.91 |
| 17 | 6200 | 55 | 0.99 | 141.18 | 138.32 | 140.06 | 6.68 |
| 18 | 6350 | 194 | 0.99 | 140.66 | 137.85 | 143.06 | 6.66 |
| 19 | 6474 | 275 | 0.99 | 143.01 | 140.21 | 150.00 | 6.73 |
| 20 | 6675 | 99 | 0.99 | 144.72 | 141.96 | 147.45 | 6.79 |
| 21 | 6827 | 58 | 0.99 | 142.83 | 140.12 | 143.19 | 6.73 |
| 22 | 6948 | 80 | 0.99 | 141.19 | 138.52 | 140.32 | 6.68 |
| 23 | 7300 | 176 | 1.00 | 140.38 | 137.86 | 141.87 | 6.66 |
| 24 | 7778 | 122 | 1.00 | 141.04 | 138.71 | 141.04 | 6.69 |

FIG. 9

| Test # k | Global Time (minutes) | Result # k | $A_k^*$ Time Averaged Glucose | Standard Deviation | Lability Factor |
|---|---|---|---|---|---|
| 41 | 12,560 | 85 | 138.05 | 60.42 | 43.77% |
| 42 | 12,617 | 55 | 137.70 | 60.98 | 44.28% |
| 43 | 12,655 | 83 | 137.47 | 60.75 | 44.19% |
| 44 | 12,775 | 80 | 136.87 | 60.57 | 44.25% |
| 45 | 13,028 | 66 | 135.47 | 60.68 | 44.79% |
| 46 | 13,379 | 176 | 135.04 | 60.38 | 44.71% |
| 47 | 13,770 | 74 | 134.72 | 60.30 | 44.76% |
| 48 | 13,873 | 125 | 134.43 | 59.66 | 44.38% |
| 49 | 14,157 | 79 | 133.70 | 59.48 | 44.49% |
| 50 | 14,480 | 144 | 133.15 | 58.91 | 44.24% |
| 51 | 14,876 | 71 | 132.39 | 58.88 | 44.48% |
| 52 | 15,132 | 169 | 132.15 | 58.58 | 44.33% |
| 53 | 15,486 | 128 | 132.57 | 58.01 | 43.76% |
| 54 | 15,614 | 120 | 132.49 | 57.48 | 43.38% |
| 55 | 15,930 | 207 | 133.17 | 57.91 | 43.49% |
| 56 | 16,386 | 227 | 135.74 | 58.83 | 43.34% |
| 57 | 16,656 | 137 | 136.56 | 58.30 | 42.69% |
| 58 | 16,909 | 105 | 136.31 | 57.90 | 42.47% |
| 59 | 17,026 | 227 | 136.53 | 58.73 | 43.01% |
| 60 | 17,381 | 345 | 139.88 | 64.33 | 45.99% |

FIG. 12

METHOD TO DETERMINE THE DEGREE AND STABILITY OF BLOOD GLUCOSE CONTROL IN PATIENTS WITH DIABETES MELLITUS VIA CREATION AND CONTINUOUS UPDATING OF NEW STATISTICAL INDICATORS

CROSS REFERENCE TO RELATED APPLICATIONS

This application is a continuation-in-part of U.S. patent application Ser. No. 11/293,534, filed on Dec. 3, 2005, which claims priority to U.S. Provisional Patent Application Ser. No. 60/632,585 filed on Dec. 3, 2004.

FIELD OF THE INVENTION

The present invention relates generally to disease management, and in particularly to a method determining the degree and stability of a blood glucose control in patients with diabetes mellitus via the creation and continuous updating of new statistical indicators such as, for example, in blood glucose monitors or free standing computers.

BACKGROUND OF THE INVENTION

A hemoglobin A1c blood test provides summarized information on blood glucose control over a 3 month period. This is the major reason for its popularity with endocrinologists and other diabetes practitioners, who do not have the time to review weeks of detailed daily blood glucose results. In healthy, non-diabetic patients, the hemoglobin A1c level is less than 5.5% of total hemoglobin, and long term studies have shown that the complications of diabetes can be delayed or even prevented if this level can be kept below 6.5%. Unlike fingerstick blood glucose tests that are readily performed by patients, the hemoglobin A1c level can only be measured in a reference laboratory or in the physician's office, making, availability an issue. Additionally, the hemoglobin A1c test can be misleading in certain medical circumstances and conditions as the test paradigm makes some assumptions that may occasionally reduce its accuracy in an evaluation of blood glucose control. Furthermore, even if the hemoglobin A1c blood test is made available to the patient for home use, this test will not replace home blood glucose monitoring, which is the only way to decide immediately whether the patient needs to modify his/her medications because of unforeseen glycemic excursions.

For home blood glucose monitoring, the control of blood glucose requires frequent fingerstick glucose testing. Typically a set of 4 to 8 tests or more per day is considered necessary for maintenance of good control for type 1 diabetes patients. Blood glucose monitors store time stamped test results and give running averages of the stored tests. The maximum amount of stored test results varies with the type of monitor, ranging from 30 data points to thousands. The running glucose average has some utility, but can be deceiving, especially for diabetes patients who suffer frequent wide swings of blood glucose from hypoglycemia (low blood glucose) to hyperglycemia (high blood glucose).

For example, if a blood glucose test is done during a hyperglycemic episode, with a blood glucose value of 190 mg/dl, followed by another glucose test during a hypoglycemia episode with a glucose value of 40 mg/dl, the 115 mg/dl average of these two tests may erroneously indicate reasonably good diabetes control and thereby, mislead the health care provider as well as the patient. Even more significantly, through a period of repeated highs and lows, the patient's diabetes may be completely out of control, and yet the average test value shown on the monitor may still be "normal." Moreover, the computation of the average blood glucose value does not take into account the time dimension. Suppose that two tests are taken within a very short time frame showing near-identical results. When computing the average test value for a series of blood glucose results including the two similar results, these two values are effectively double counted, with a resulting averaging bias.

Frequently, when patients find blood glucose results outside the normal range, they repeat the blood, test immediately (to make sure that it was correct the first time), and a distorted running average is calculated by meter software. A high (or low) blood glucose situation lasting a long time will have a more significant impact on the patient's health than high or low glucose levels persisting for only a short time. So it is imperative to take into account the time elapsed between the tests, which a traditional running glucose average does not do. Thus, in spite of being the most common statistic reported on blood glucose monitors today, the average glucose calculation often supplies information of limited utility and may be downright misleading. In today's blood glucose meters, there is no statistical construct which offers a time-normalized "snapshot view" of glycemic control. Patients, physicians and health care managers need a more sophisticated statistical analysis of glycemic control in order to make informed decisions about diabetes management.

SUMMARY OF THE INVENTION

Based on the foregoing limitations of the prior art, the present invention provides new computed statistical indicators to assess the blood glucose control of patients with diabetes over a period of time (e.g., days, weeks, months), and allows for the incorporation and the computation of these indicators in devices such as, for example, blood glucose monitors or free standing computers.

In accordance with one exemplary embodiment, a method for determining a stability of a blood glucose concentration of a patient is disclosed. The method comprises providing a plurality of blood glucose concentration test results each taken from the patient at a different time over a time period; approximating a plurality of blood glucose concentration test result values as functions of time from consecutive ones of the plurality of blood glucose concentration test results; and computing a time averaged glucose value as a first indicator by averaging the approximated blood glucose concentration test result values over the time period. The method further includes applying a time-based weight to each of the blood glucose concentration test results by multiplying each of the blood glucose concentration test results by a respective coefficient; computing a weighted average by averaging the time-based weighted blood glucose concentration test results; and computing a simulated measurement of a blood hemoglobin as a second indicator by correlating with a pre-determined formula the weighted average of the time-based weighted blood glucose concentration test results and the blood hemoglobin. The method also comprises computing a variance of the blood glucose concentration test results; computing a standard deviation of the variance of the blood glucose concentration test results; computing a ratio of the standard deviation to the time averaged glucose value to give a third indicator representing variability of blood glucose concentration over the time period; and providing the first, second, and third indicators.

Optionally, at least one of the steps of the method may be performed in a recursive manner. Further, it is contemplated that a trapezoidal rule of the family of Newton-Cotes formulas may be used to approximate the blood glucose concentration test result values. Also, the multiplying coefficients of the blood glucose concentration test results may be functions of the time the respective blood glucose concentration test result was taken relative to a start time of the time period such that blood glucose concentration test result values are given progressively lower time-based weights as the times the blood glucose concentration test results were taken approach the start time of the time period. Further, the pre-determined formula correlating the average of time-based weighted blood glucose concentration test results and the blood hemoglobin may be a linear regression formula. In addition, the blood hemoglobin measured through simulation may be blood hemoglobin A1c. Moreover, the ratio may be represented as a percentage.

In accordance with another exemplary embodiment, a system for determining a stability of a blood glucose concentration of a patient comprises a processor. This processor may be programmed to receive a plurality of blood glucose concentration test results each taken from the patient at a different time over a time period and to compute a time-averaged glucose parameter through an averaging of approximated blood glucose concentration test result values as functions of time, the time-averaged glucose parameter being indicative of blood glucose concentration control over the time period. In addition, the processor may be programmed to compute a virtual blood hemoglobin parameter through a simulated measurement of a blood hemoglobin through a pre-determined formula correlating an average of time-based weighted blood glucose concentration test results and the blood hemoglobin, the virtual blood hemoglobin parameter being indicative of blood glucose concentration control over an extended time period encompassing the time period. Also, the processor may be programmed to compute a lability factor parameter through a ratio of a standard deviation of a variance of the blood glucose concentration test results to the approximated blood glucose concentration test result values average, the lability factor parameter being indicative of a variability in blood glucose concentration over the time period, and provide the time-averaged glucose parameter, the virtual blood hemoglobin parameter, and the lability factor parameter.

Optionally, the processor may be programmed to compute at least one of the time-averaged glucose parameter, the virtual blood hemoglobin parameter, and the lability factor parameter in a recursive manner. Further, the time-averaged glucose parameter may be computed by the processor determining the blood glucose concentration test result values with consecutive blood glucose concentration test results separated by time intervals; approximating the blood glucose concentration test result values with a rule of a family of Newton-Cotes formulas; and averaging the approximated blood glucose concentration test result values over the time period. It is contemplated that a trapezoidal rule of the family of Newton-Cotes formulas may be used to approximate the blood glucose concentration test result values. The virtual blood hemoglobin parameter is computed by the processor applying a time-based weight to each of the blood glucose concentration test results by multiplying each of the blood glucose concentration test results by a respective coefficient; averaging the time-based weighted blood glucose concentration test results; and correlating with the pre-determined formula the average of time-based weighted blood glucose concentration test results and the blood hemoglobin. The lability factor parameter is computed by the processor computing a variance of the blood glucose concentration test results; computing a standard deviation of the variance of the blood glucose concentration test results; and computing the ratio of the standard deviation to the approximated blood glucose concentration test result values average. In addition, the system may further comprise a user interface to display at least one of the computed time-averaged glucose parameter, the computed virtual blood hemoglobin parameter, and the computed lability factor to the patient. It is further contemplated that the system may be provided to a blood glucose meter or to a computer. Further, the processor may be programmed to receive the plurality of glucose measurements from memory, wherein the memory may be external to the system.

In accordance with yet another embodiment, a computer-usable medium is disclosed. The computer-usable medium provides computer readable instructions for execution by a processor to perform a method comprising approximating a plurality of blood glucose concentration test result values as functions of time from consecutive ones of a plurality of blood glucose concentration test results; computing a time averaged glucose value as a first indicator by averaging the approximated blood glucose concentration test result values over the time period; applying a time-based weight to each of the blood glucose concentration test results by multiplying each of the blood glucose concentration test results by a respective coefficient; computing a weighted average by averaging the time-based weighted blood glucose concentration test results; computing a simulated measurement of a blood hemoglobin as a second indicator by correlating with a pre-determined formula the weighted average of the time-based weighted blood glucose concentration test results and the blood hemoglobin; computing a variance of the blood glucose concentration test results; computing a standard deviation of the variance of the blood glucose concentration test results; computing a ratio of the standard deviation to the time averaged glucose value to give a third indicator representing variability of blood glucose concentration over the time period; and providing the first, second, and third indicators.

These and other advantages and features of the invention will become apparent in the following discussions, drawings, and claims.

BRIEF DESCRIPTION OF THE DRAWINGS

FIG. 2 is a depiction of a summary output showing parameters Time-Averaged Glucose, Virtual A1c and Lability Factor calculated according to the present invention.

FIG. 9 is a table showing results of a step by step computation of A* and of VA1c according to the present invention.

FIG. 12 is a table showing result of computations of the variance, the standard deviation and the Lability Factor according to methods of the present invention.

DETAILED DESCRIPTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriate detailed structure.

Figure 1:
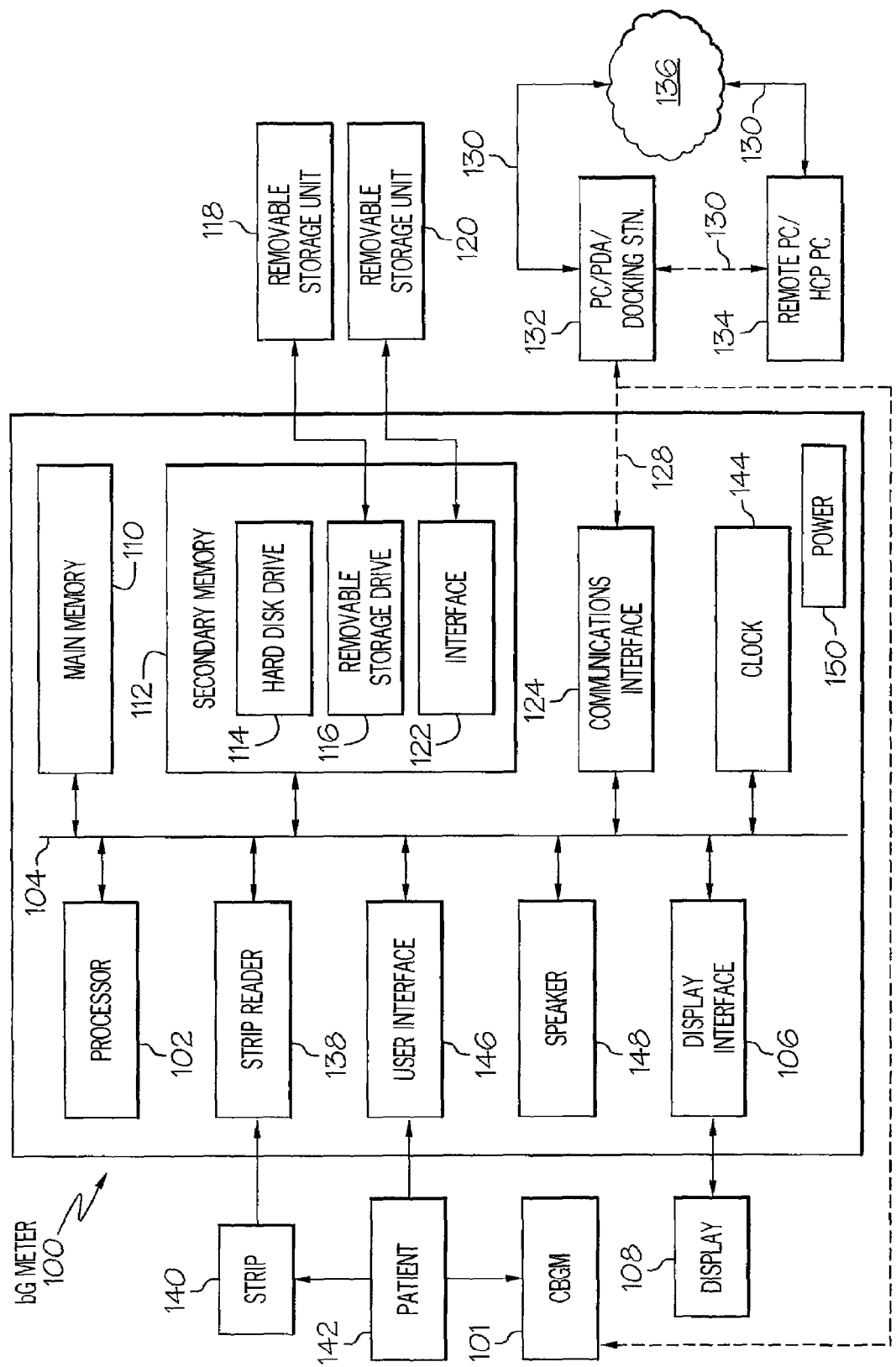
FIG. 1 is a block diagram of one embodiment of a processor based system for implementation of the present invention.

FIG. 1 is a block diagram of one embodiment of a processor based system for implementation of the present invention. The present invention may be implemented using hardware, software or a combination thereof and may be implemented in one or more microprocessor based systems, such as a portable computer or other processing systems, such as personal digit assistants (PDAs), or directly in self-monitoring blood glucose devices or meters (bG meters) equipped with adequate memory and processing capabilities to process a chronological sequence of measurements of a time dependent parameter measured in or on the human body, namely of the glucose level (e.g. the blood glucose (bG) level).

In an example embodiment, algorithms and routines according to the present invention are implemented in software running on a self-monitoring blood glucose (bG) meter 100 as illustrated in FIG. 1. The algorithms and routines are discussed in greater detailed hereafter in later sections. The bG meter 100 is common in the industry and includes essentially any device that can functions as a blood glucose acquisition mechanism. The bG meter 100 or acquisition mechanism, device, tool, or system includes various conventional methods directed toward drawing a blood sample (e.g. by finger prick) for each test, and making a spot determination of the glucose level using an instrument that reads glucose concentrations by optical, electrochemical, electromechanical or calorimetric detection/measurement methods. In addition, the bG meter 100 may include indwelling catheters and subcutaneous tissue fluid sampling devices and/or communicate with devices, such as continuous blood glucose monitor (CBGM) 101, having indwelling catheters and subcutaneous tissue fluid sampling devices.

In the illustrated embodiment, the bG meter 100 includes one or more microprocessors, such as processor 102, which is connected to a communication bus 104, which may include data, memory, and/or address buses. The bG meter 100 may include a display interface 106 providing graphics, text, and other data from the bus 104 (or from a frame buffer not shown) for display on a display 108. The display interface 106 may be a display driver of an integrated graphics solution that utilizes a portion of main memory 110 of the meter 100, such as random access memory (RAM) and processing from the processor 102 or may be a dedicated graphics card. In another embodiment, the display interface 106 and display 108 additionally provide a touch screen interface for providing data to the bG meter 100 in a well known manner.

Main memory 110 in one embodiment is random access memory (RAM), and in other embodiments may include other memory such as a ROM, PROM, EPROM or EEPROM, and combinations thereof. In one embodiment, the bG meter 100 includes secondary memory 112 which may include, for example, a hard disk drive 114 and/or a removable storage drive 116, representing a floppy disk drive, a magnetic tape drive, an optical disk drive, a flash memory, etc. The removable storage drive 116 reads from and/or writes to a removable storage unit 118 in a well known manner. Removable storage unit 118, represents a floppy disk, magnetic tape, optical disk, etc. which is read by and written to by removable storage drive 116. As will be appreciated, the removable storage unit 118 is thus a computer usable medium having stored therein computer software and/or data as well as the computer instructions to execute the processes of the present invention. Likewise such computer instructions may be provides in other computer usable mediums such as for example, memory 110, drive 114, unit 120, and even as signals 128, 130, 134 from the bG meter 100, the remote PC 134 or the network 136 in still other embodiments.

In alternative embodiments, secondary memory 112 may include other means for allowing computer programs or other instructions to be loaded into the bG meter 100. Such means may include, for example, a removable storage unit 120 and an interface 122. Examples of such removable storage units/interfaces include a program cartridge and cartridge interface, a removable memory chip (such as a ROM, PROM, EPROM or EEPROM) and associated socket, and other removable storage units 120 and interfaces 122 which allow software and data to be transferred from the removable storage unit 120 to the bG meter 100.

The bG meter 100 in one embodiment includes a communications interface 124. The communications interface 124 allows software and data to be transferred between the bG meter 100 and an external device(s) 126. Examples of communications interface 124 may include one or more of a modem, a network interface (such as an Ethernet card), a communications port (e.g., USB, firewire, serial or parallel, etc.), a PCMCIA slot and card, a wireless transceiver, and combinations thereof. In one embodiment, the external device 126 is a personal computer (PC), and in another embodiment is a personal digital assistance (PDA). In still another embodiment, the external device 126 is a docking station wherein the communication interface 124 is a docket station interface. In such an embodiment, the docking station 126 may provided and/or connect to one or more of a modem, a network interface (such as an Ethernet card), a communications port (e.g., USB, firewire, serial or parallel, etc.), a PCMCIA slot and card, a wireless transceiver, and combinations thereof. Software and data transferred via communications interface 124 are in the form of wired or wireless signals 128 which may be electronic, electromagnetic, optical, or other signals capable of being sent and received by communications interface 124. For example, as is known, signals 128 may be sent between communication interface 124 and the external device(s) 126 using wire or cable, fiber optics, a phone line, a cellular phone link, an RF link, an infrared link, other communications channels, and combinations thereof.

In one embodiment, the external device 126 is used for establishing a communication link 130 between the bG meter 100 and still further electronic devices such as a remote Personal Computer (PC) of the patient, and/or a health care provider (HCP) computer 134, directly or indirectly, such as through a communication network 136, such as the Internet and/or other communication networks. The communication interface 124 and/or external device(s) 126 may also be used to communicate with further data gathering and/or storage devices such as insulin delivering devices, cellular phones, personal digital assistants (PDA), etc. Specific techniques for connecting electronic devices through wired and/or wireless connections (e.g. USB and Bluetooth, respectively) are well known in the art.

In the illustrative embodiment, the bG meter 100 provides a strip reader 138 for receiving a blood glucose test strip 140. The test strip 140 is for receiving a blood sample from a patient 142, which is read by the strip reader 138. Data, representing the information provided by the test strip, is provided by the strip reader 138 to the processor 102 which executes a computer program stored in memory 110 to perform various calculations as discussed in great detail below on the data. The results of the processor 102 from using the data is displayed on the display 108 and/or recorded in secondary memory 110, which is herein referred to as self monitored blood glucose (bG) data. The bG data may include, but not limited thereto, the blood glucose values of the patient 142, the insulin dose values, the insulin types, and the parameter values used by processor 102 to calculate future blood glucose values, supplemental insulin doses, and carbohydrate supplements. Each blood glucose value and insulin dose value is stored in memory 112 with a corresponding date and time. An included clock 144 of the bG meter 100 supplies the current date and time to processor 102.

The bG meter 100 further provides a user input device(s) 146 such as keys, touchpad, touch screen, etc. for data entry, program control, information requests, and the likes. A speaker 148 is also connected to processor 102, and operates under the control of processor 102 to emit audible alerts/reminders to the patient, such as for example, to take a meal, of possible future hypoglycemia, and the likes. A suitable power supply 150 is also provided to power the bG meter 100 as is well known to make the meter portable.

The terms "computer program medium" and "computer usable medium" are used to generally refer to media such as removable storage drive 116, a hard disk installed in hard disk drive 114, signals 128, etc. These computer program products are means for providing software to bG meter 100. The invention includes such computer program products.

Computer programs (also called computer control logic) are stored in main memory 110 and/or secondary memory 112. Computer programs may also be received via the communications interface 124. Such computer programs, when executed, enable the bG meter 100 to perform the features of the present invention as discussed herein. In particular, the computer programs, when executed, enable processor 102 to perform the functions of the present invention. Accordingly, such computer programs represent controllers of bG meter 100.

In an embodiment where the invention is implemented using software, the software may be stored in a computer program product and loaded into bG meter 100 using removable storage drive 116, removable storage unit 120, hard drive 114, or communications interface 124. The control logic (software), when executed by the processor 102, causes the processor 102 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described hereafter are implemented in the C++ programming language, but could be implemented in other programs such as, but not limited to, Visual Basic, C, C#, Java or other programs available to those skilled in the art.

As mentioned above, the bG meter 100 is used by the patient 142 for recording, inter alia, insulin dosage readings and spot measured blood glucose levels. Such bG data obtained by the bG meter 100 in one embodiment is transferable via the communication interface 124 to another electronic device, such the external device 126 (PC, PDA, or cellular telephone), or via the network 136 to the remote PC and/or HCP computer 134. Examples of such bG meters include but not limited to, the Accu-Chek Active meter and the Accu-Chek Aviva system both by Roche Diagnostics, Inc. which are compatible with the Accu-Chek CAMIT Pro and the Accu-Chek Compass software to download test results to a personal computer or the Accu-Chek Pocket Compass Software for downloading and communication with a PDA.

Accordingly, it is to be appreciated that the bG meter 100 includes the software and hardware necessary to process, analyze and interpret the self-recorded diabetes patient (i.e., bG) data in accordance with predefined flow sequences (as described below in detail) and generate an appropriate data interpretation output. In one embodiment, the results of the data analysis and interpretation performed upon the stored patient data by the bG meter 100 are displayed in the form of a report, trend-monitoring graphs, and charts to help patients manage their physiological condition and support patient-doctor communications. In other embodiments, the bG data from the bG meter 100 may be used to generated reports (hardcopy or electronic) via the external device 126 and/or personal computer (PC) and/or HCP computer 134.

The bG meter 100 further provides the user and/or his or her HCP with the possibilities of a) editing data descriptions, e.g. the title and description of a record; b) saving records at a specified location, in particular in user-definable directories as described above; c) recalling records for display; d) searching records according to different criteria (date, time, title, description etc.); e) sorting records according to different criteria (values of the bG level, date, time, duration, title, description etc.); f) deleting records; g) exporting records; and/or h) performing data comparisons as is well known.

It is to be appreciated that the present invention enhances existing software and/or hardware that retrieves and processes the bG data. The methods and system of the invention can be directly incorporated into existing home blood glucose monitors, or used for the enhancement of software that retrieves and processes bG data, by introducing a process for calculating new computed statistical indicators to assess the blood glucose control of patients with diabetes using data from blood glucose tests conducted over a period of time. The time period may be a few months in one embodiment, and in other embodiments may be shorter, such as a few days or weeks. In still other embodiments, the specific time period may be determined and set by a health care provided for each particular patient on the device implementing the invention. The statistical indicators computed according to the present invention is discussed hereafter.

The indicators computed from blood glucose test results include a Time Averaged Glucose (TAG) parameter, a simulation of the measurement of hemoglobin A1c called the Virtual A1c (VA1c), and an indicator of blood glucose variability called the Lability Factor (LF). These indicators are functions of the patient's blood glucose test results over a specific period of time, as well as of the elapsed times between all these tests. It is to be appreciated that all these indicators in one embodiment are computed using a microprocessor in a typical blood glucose meter without any need for increased processing power.

The first new indicator is a Time-Averaged Glucose (TAG) value, which is a mathematical approximation of a function over a time period to give an indication of the blood glucose control normalized for the time interval between glucose tests. The second new indicator is the Virtual Hemoglobin A1c (VA1c), which mimics the measurement of the blood hemoglobin A1c (HgbA1c), and simulates the actual measurement of HgbA1c in the blood over a specific window of time. Finally, the third indicator is called the Lability Factor, which is a ratio of the standard deviation of the test-values during that period of time, to the Time Averaged Glucose-over the period of time, and allows patients, physicians and health plan managers to assess the degree of blood glucose variability over time. Blood glucose lability has recently been recognized to be an independent risk factor for diabetes related microvascular complications. In addition, the Lability Factor allows for an independent assessment of the reliability and accuracy of the Time Averaged Glucose and the Virtual A1c.

The invention will make use of the information already captured in the blood glucose monitor to produce a meaningful and constantly updated summary of the control of the blood glucose for the patient and for the physician. For example, FIG. 2 is a depiction of an output which may be provided by bG meter 100 on display 108 (FIG. 1). The output in one embodiment is a control summary 200, shows in tabular format and entitled "Results", which provides the indicators Time-Averaged Glucose, Virtual A1c, and Lability Factor which have been calculated according to the present invention for a specific period of time and based on the blood glucose tests performed and stored in the patients' blood glucose monitor. The summary 200 in addition to the above mentioned indicators may also provide a traditional average value of the tests during the period of time as provided currently in most blood glucose meters. In one embodiment, the period of time is provided without the time dimension. In meters implementing the present invention, the traditional average will be qualified by Indicator #1 (Time Averaged Glucose). In another embodiment, the output may also include guidelines 202, also shown in tabular format and entitled "Guideline," to help a patient understand what the indicators are indicating in the control summary 200.

It is to be appreciated that a running glucose average, by itself, is not a good indication of glycemic control. So to enhance all the collected and processed blood glucose data, the present invention uses the Time Averaged Glucose and the Virtual A1c as indices of "tightness of control." Although the standard deviation of the blood glucose (already implemented in some currently available diabetes management software) provides one measure of the variation around the average value, the Lability Factor (ratio of standard deviation to the Time Averaged Glucose as a percentage) is used instead since in this application the Time Averaged Glucose is the gold standard. A "low" percentage indicates less variable blood glucose values and also lends credence to the Time Averaged Glucose and Virtual A1c calculations (i.e. in this case the function $\Psi(t)$ has a relatively low number of small "peaks and valleys").

Figures 3, 4:
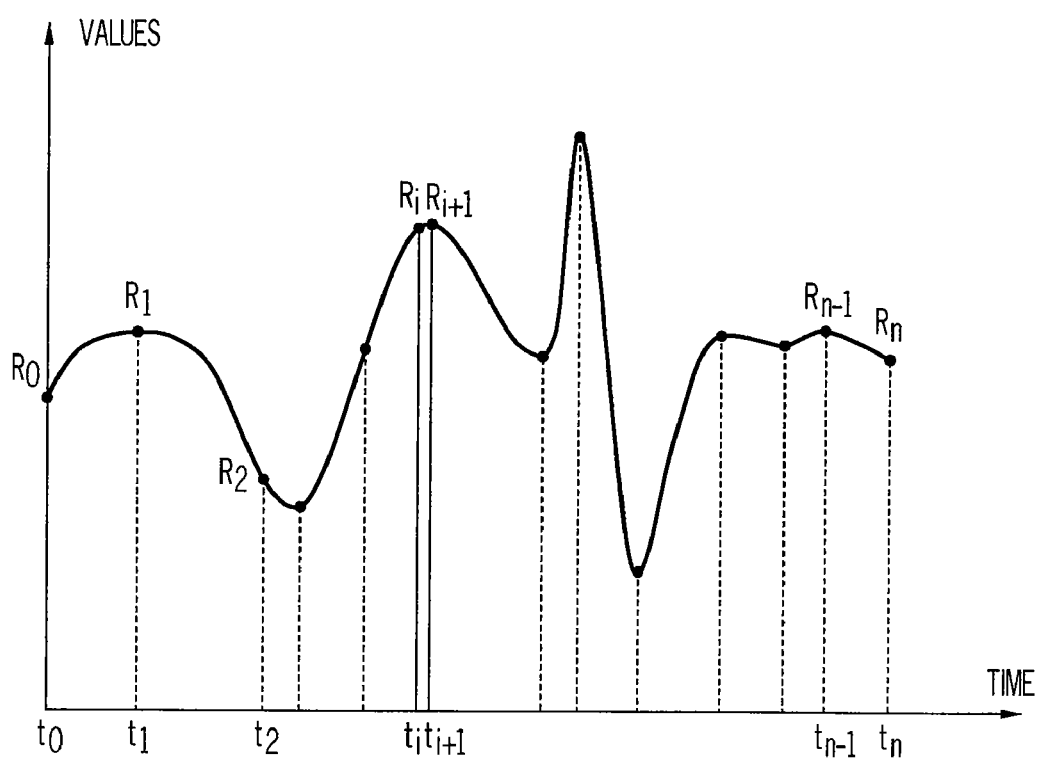
FIG. 3 is a table showing a relationship between hemoglobin A1c percentages and average plasma glucose concentrations according to the present invention.
FIG. 4 is a plot representation of a function $\Psi(t)$ representing glucose concentration in blood as a function of time.

Adjunctive testing of hemoglobin A1c is highly recommended (every 3 months) for independent assessment of the glycemic control in type 1 and type 2 diabetes and for calibration of the Virtual A1c. Tables exist which 1) specify the level of control and 2) map the percentage of A1c hemoglobin to the mean blood glucose of the patient. FIG. 3 shows one of these tables which shows the relationship between hemoglobin A1c percentages and average plasma glucose concentrations.

Unfortunately, the hemoglobin A1c test is available only in physician offices and reference labs and has fundamental scientific flaws. The hemoglobin A1c test does not take hypoglycemic episodes into account, but actually gives a "better" result because of low blood glucose events. Like the running average of blood glucose test results, the hemoglobin A1c decreases with hypoglycemic incidents of significant frequency or duration.

Since hemoglobin A1c is a direct product of the binding of ambient glucose to the hemoglobin pigment in red blood cells and since the red cells have a typical average half life in the range of 50-55 days, there are 3 negative consequences which diminish the validity of the hemoglobin A1c measurement: a) HgbA1c is necessarily weighted by more recent blood glucose values in the blood, b) HgbA1c does not provide information on glycemic control more than 3 months prior and c) HgbA1c is not accurate if red cell survival is altered by disease states such as renal failure, liver failure, hemoglobinopathy, blood loss, or severe illness.

Consequently, quarterly hemoglobin A1c tests are may be used to quantify the evolution and the control of the disease (hemoglobin A1c tests are typically ordered every 3 months by diabetes professionals). Such testing may give an erroneously favorable impression of glycemic control in patients with anemia, liver disease and kidney disease resulting in under treatment. Patients with abnormal hemoglobin molecules that electophoretically migrate in the same band as HgbA1c may exhibit artificially elevated hemoglobin A1c values that could lead well intentioned health care providers to overtreat.

The embodiments of the present invention addresses these problems. If the blood glucose tests, on which these indicators are based, are sufficient in number and collected in the required time interval, then the methods of the present invention will provide an accurate summary of the control-of blood glucose during that specific period. The following section provides the mathematical definition of these indicators.

Indicator #1—Time Averaged Glucose: A Mathematical Average of the Test Value as a Function of Time.

If $\Psi(t)$ is the test result value as a function of time, and if an average (A) of this function is computed over the period of time $t_0$ to $t_n$, then the average (A) is given by equation (1) as follows:

$$A = \frac{1}{t_n - t_0} \int_{t_0}^{t_n} \Psi(t) dt. \tag{1}$$

Note that in this application the function $\Psi(t)$ is not continuous and is only defined on the test times $t_0, t_1, \ldots, t_n$ where it takes the values: $R_0, R_1, \ldots, R_n$. FIG. 4 is a plot representation of the hypothetical function $\Psi(t)$ representing the value of the glucose in the blood as a function of time. In the illustrated embodiment such data may be measured and collected by a continuous glucose metering device; however, in other embodiments data collected by a non-continuous blood glucose meter via a plurality of test strips readings may also be used. In the illustrated embodiment, the continuous function is represented by a solid line and is sampled at the times $t_0, t_1, \ldots t_n$ where it will take the values $r_0, r_1, \ldots, r_n$ given by the tests. Values outside of these test points may or may not be known.

Figure 5:
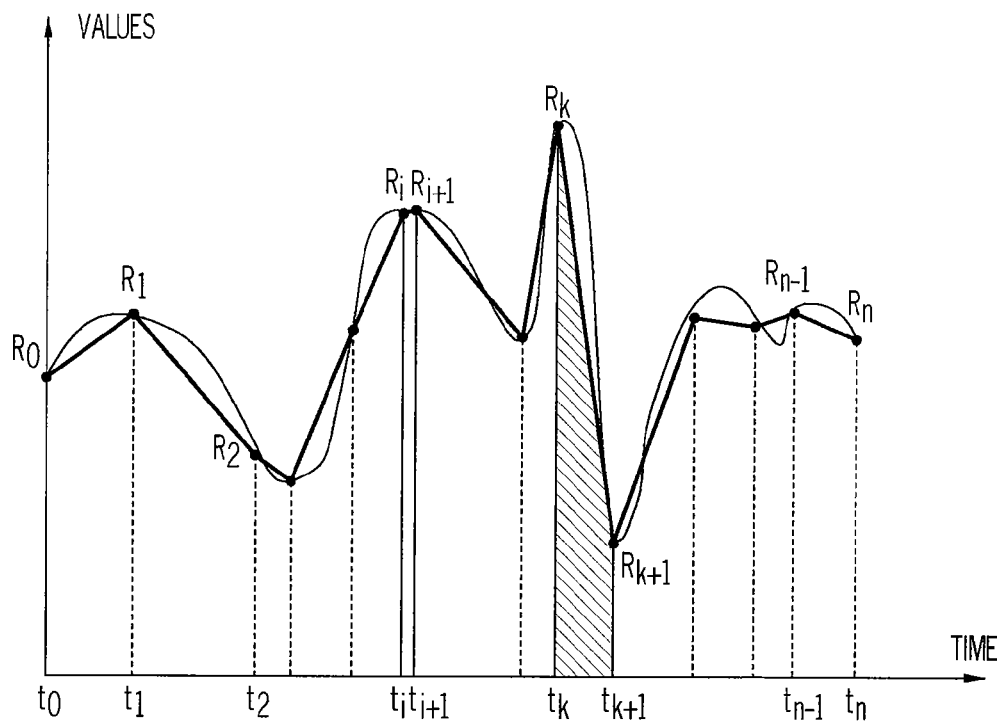
FIG. 5 is a plot representation showing approximation of the $\Psi(t)$ function of FIG. 4.

FIG. 5 is another plot representation showing how the function Ψ(t) is approximated by a sequence of segments joining the various known test points. The integral may be approximated by any of the closed type Newton-Cotes formulas, including, but not limited to, the trapezoidal rule, Simpson's rule, and Boole's rule. For example, in the illustrated embodiment, the integral $$\int_{t_0}^{t_n} \Psi(t)\,dt$$

is approximated by the trapezoidal rule. In this example, the area ($A_k$) of the trapezoid corresponding to test points $R_k$ and $R_{k+1}$ has a value this is defined by equation (2):

$$A_k = \frac{1}{2}(R_k + R_{k+1})(t_{k+1} - t_k), \quad (2)$$

where k=0, 1, . . . n−1 and therefore by substituting equation (2) into equation (1), the average (A*) of the approximated function Ψ(t) between $t_0$ and $t_n$ may be represented by equation (3) as:

$$A^* = \frac{1}{2(t_n - t_0)} \sum_{k=0}^{n-1} (R_k + R_{k+1})(t_{k+1} - t_k). \quad (3)$$

The value of A*, the mathematical average of the test value as a function of time over the time period, is used as the Indicator #1, the "Time Averaged Glucose." In other embodiments, the area ($A_k$) may be more accurately calculated by dividing the interval of integration between the test points into smaller subintervals, and then applying the trapezoidal rule on each of them. The result of this composite trapezoidal rule embodiment is then used to provide a more accurate value of the time period average (A*) if the cost of computing is not a factor and/or if such increased accuracy is a desired. It is further contemplated that in other embodiments other rules, methods, or formulas, such as the Simpson's rule or Boole's rule referenced above and combinations thereof, may be used for integral or parabolic approximations and, in fact, to provide even more accurate approximations than those offered by the trapezoidal rule.

Indicator #2—Virtual Hemoglobin A1c

As indicated earlier, a new index, Virtual Hemoglobin A1c (VA1c) is defined to mimic the measurement of hemoglobin A1c in the blood. To compute VA1c over a specific sliding window of time, the integral of the function "test result value" vs. time is used with the blood glucose test values during the specific period. Generally and in one embodiment, a three (3) month period is the recommended length of time required if one wants to follow the actual creation of hemoglobin A1c in the blood, but unlike hemoglobin A1c, VA1c as well as the time period average A* can be evaluated over a period of arbitrary length in other embodiments.

Figure 6:
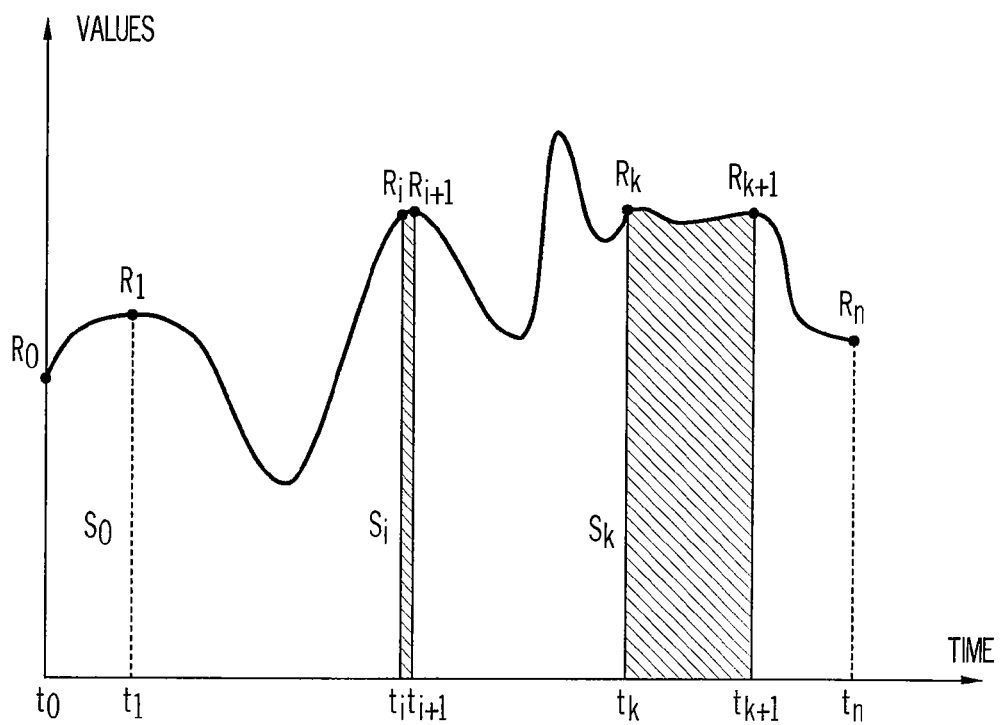
FIG. 6 is a plot representation shows impact of time on both average test value and on computation of VA1c according to the present invention.

FIG. 6 shows the impact of time on both the average test value and on the computation of VA1c. It shows the different effect of two sets of two consecutive blood glucose tests $R_i$, $R_{i+1}$ and $R_k$, $R_{k+1}$ on the VA1c as well as their impact on the average blood glucose calculation. It is to be appreciated that the longer a patient remains in a hyperglycemic situation, the more significant will be the impact on his/her VA1c. Accordingly, in one embodiment, the method eliminates the "double counting" of tests close in time and in another embodiment, the method simulates the natural creation of hemoglobin A1c in the blood.

Figure 7:
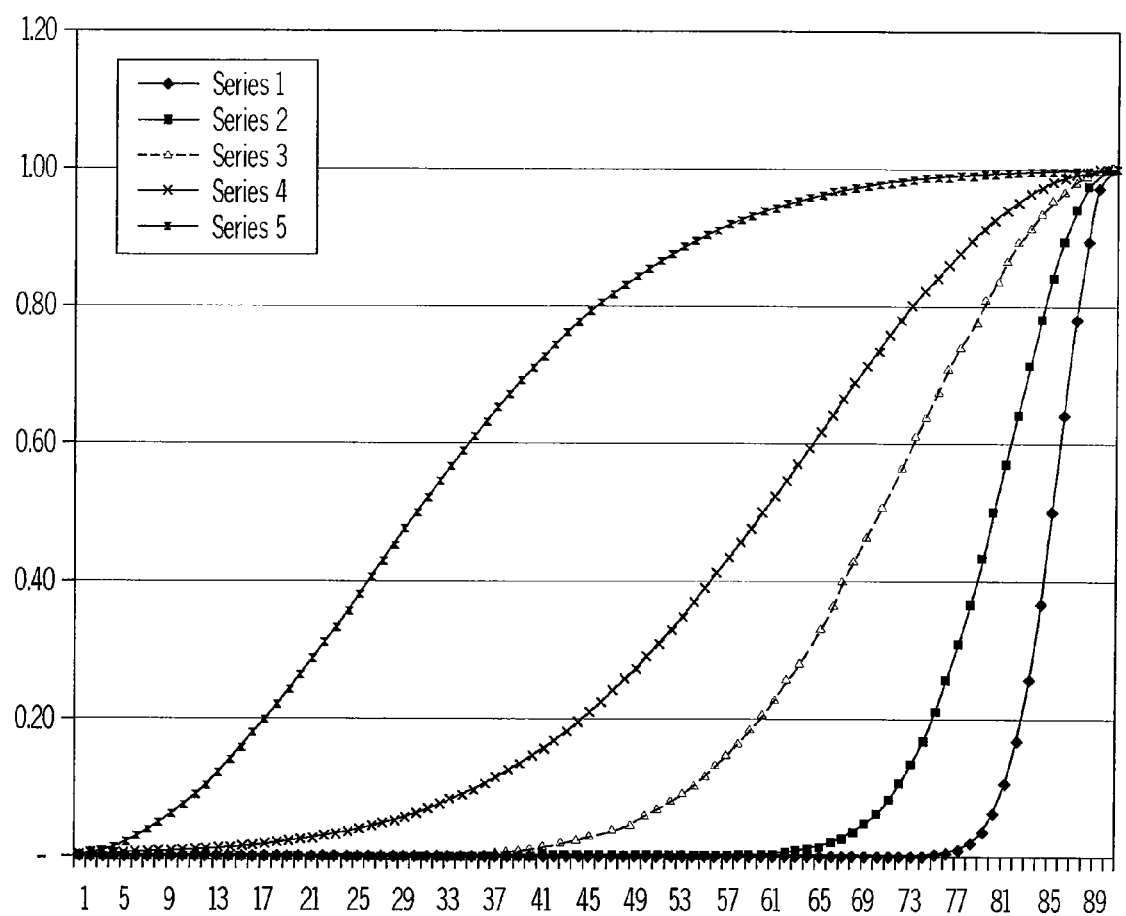
FIG. 7 is a plot showing a family of curves which are used to provide $\gamma$ coefficients which are applied to test results according to an embodiment of the present invention

For example, as exposed in FIG. 6, if 2 (or more) consecutive, high blood glucose tests $R_k$ and $R_{k+1}$ are separated by a long period of time, their contribution to VA1c is higher than if these consecutive tests are separated by a shorter period of time like tests $R_i$ and $R_{i+1}$. As such, in one embodiment, each test result $R_k$ is weighed by a coefficient γ, which is an increasing function of the distance in time between the beginning of the period and the time of the actual test. This γ coefficient varies between 0 and 1. The tests given at the start of the period have a multiplying coefficient close to 0, and the most recent tests (those given at the end of the period), have their multiplying coefficient close to 1. In one embodiment, the period T is set to 3 months (e.g., 90 days) to simulate the natural decay of human red blood cells. In other embodiments, the period T may be set to any other length, such as may be determined by a health care provided for each particular patient. FIG. 7 shows a graphical representation of some functions that are well suited to represent the natural decay of the blood cells. These functions belong to the same mathematical family and are parameterized. Two variations are used, where the first variation is defined by equation (4) as follows:

$$\gamma(d) = \alpha^{-\left(\frac{T-d}{\beta}\right)^2}, \quad (4)$$

where γ is a function of the variable d (for day number), T=90 days, and where α and β are parameters selected to give the best VA1c approximation of the actual hemoglobin A1c results. The second variation is defined by equation (5) which is as follows:

$$\gamma(d) = 1 - \alpha^{-\left(\frac{d}{\beta}\right)^2}. \quad (5)$$

In this latter embodiment, the γ coefficient is a function of the date when the test is done, relative to the start of the test period. For the aforementioned simulation it is sufficient to measure γ in days, but it could be expressed in smaller time units if desired. For example if the selected period T is 90 days, one can have a sequence of γ coefficients like $\gamma_1$, $\gamma_2, \ldots, \gamma_{90}$ where the $\gamma_n$ coefficient applies to all the test results of day n.

Consequently, the indicator VA1c is derived from equation (3) by factoring in the half life of blood cells with each test result $R_k$. This is accomplished by multiplying each test result by the coefficient $\gamma_j$ with the weight satisfying the relations $0 \leq \gamma_j \leq 1$ and $\gamma_j \leq \gamma_{j+1}$, where j indicates the day of test and k the number of the test result. Accordingly, to compute the indicator VA1c the same approach as for time period average A* is used but $R_k + R_{k+1}$ is replaced by their weighted values $\gamma_{j,k} R_k + \gamma_{j,k+1} R_{k+1}$ where k represents the test number and j the day of the test. The following equation (6) provides the weighted average C* of the tests (i.e., weighted by the $\gamma_{j,k}$ coefficients) as follows:

$$C^* = \frac{1}{2(t_n - t_0)} \sum_{k=0}^{n-1} (\gamma_{j,k} R_k + \gamma_{j,k+1} R_{k+1})(t_{k+1} - t_k). \quad (6)$$

In order to emulate hemoglobin A1c, a linear regression formula correlating average glucose and hemoglobin A1c that is accepted worldwide by diabetes practitioners and approved by the ADA is applied. This linear relation between a test value average ($\mu$), e.g. a mean bG value obtained from a blood glucose meter, and A1c, developed from large scale diabetes treatment trials, is $\mu=33$A1c$-82$ or as rewritten as equation (7) as follows:

$$A1c = \frac{\mu}{33} + \frac{82}{33}, \quad (7)$$

where $\mu$ is in units of mg/dL. It is to be appreciated, however, equation (7) may change as it is updated by the ADA.

Accordingly, combining equations (6) and (7) by equating the test value average $\mu$ to the weighted average $C^*$, the indicator VA1c is represented by equation (8) as follows:

$$VA1c = \frac{1}{66(t_n - t_0)} \sum_{k=0}^{n-1} (\gamma_{j,k} R_k + \gamma_{j,k+1} R_{k+1})(t_{k+1} - t_k) + \frac{82}{33}. \quad (8)$$

As indicated before, the notation $\gamma_{j,k}$ indicates that the $\gamma$ coefficient is a function of the date on which the $k^{th}$ test was performed. Equation (8) does not lend itself to a formal recursive calculation since the $\gamma$ coefficient depends on a different variable than its rank, specifically, the time interval from the origin of the time frame selected. As a result, the evaluation of the indicator VA1c in a general purpose computer may use equation (8) with the $\gamma$ coefficients directly computed (several functions can be used to approximate the exponential decay of the red cells). In a limited processing environment, like a blood glucose meter, it is appropriate to use a different approach where the $\gamma$ coefficient values are directly extracted from a table based on the age (i.e., date and/or time) of the test.

It is also important to note that if the linear relation between the test value average $\mu$ and A1c changes, or even if this relation is not expressed as a linear relation, the indicator VA1c will still be a direct function of the weighed average $C^*$, and thus only equation (8) will need to be changed (the coefficients of the linear relation between the average glucose value and HgA1c have already been modified several times in the last few years). The method to compute the indicator VA1c, explained later, will remain entirely applicable.

Indicator #3—Lability Factor: The "Measure" of Glycemic Variability

To make the concept of measured glycemic variability more interpretable by lay persons and health care providers alike, the Lability Factor is defined as a ratio of the standard deviation between the test results $R_i$ and their average provided over the time period average $A^*$ of the test values and expressed as a percentage. If the term $\mu_n$ is the average of the test values for the test period $t_0$ and $t_n$, then the standard deviation (E) of the test values is given by equation (9) as follows:

$$E = \sqrt{\frac{\sum_{i=0}^{n} (R_i - \mu_n)^2}{n}}, \quad (9)$$

and indicator #3, the Lability Factor (Q), is thus given by equation (10) as follows:

$$Q = \frac{E}{A^*}(100\%). \quad (10)$$

In one embodiment, equations (3), (8), and (10) are directly programmed on a general purpose computer to yield the calculation of the three indicators, namely Time-Averaged Glucose, Virtual A1c, and Lability Factor, respectively. In such an embodiment, the computer will have the capability of downloading test data (value of the test and date/time of the test) from a patient's blood meter. In other embodiments, the present invention include implementations as microcode, software or firmware such as, for example, inside a blood glucose meter, a continuous blood glucose meter, pda, cell phone, insulin pump, other such portable devices and/or computer readable medium. In such embodiments, any or all of the indicators can be displayed each time the device is turned on, and/or on demand. In one embodiment, the indicators are updated after every blood glucose test. Methods designed for a portable device implementation such as, for example, a blood glucose meter are now discussed hereafter.

A recursive method is used to compute the standard deviation and other indicators in order to minimize the required processing power and memory of the device used. This is an important consideration when the device is a portable device with limited processing power and memory such as for example, a blood glucose meter, but only of marginal importance if the device is a general purpose computer.

Method to Compute Indicator #1. Time Averaged Glucose

This iterative method is utilized to compute indicator #1 which represents the mathematical average of the test value as a function of time. As seen earlier, the Time-Averaged Glucose value $A^*$ is given by equation (3). As such, for example, after completion of test number k at time $t_k$, the value of the indicator value $A^*$ can be represented by equation (11) as follows:

$$A_k^* = \frac{\sum_{i=0}^{k-1} S_i}{(t_k - t_0)}, \quad (11)$$

where $k=1, 2, \ldots, n$, where $S_i$ is the area of the trapezoid approximating the integral of the $\Psi(t)$ function between tests $R_i$ and $R_{i+1}$, and where $t_0$ is the time of the first test (i.e., $k=1$). The area $S_i$ is thus given by equation (12) as follows:

$$S_i = \frac{1}{2}(t_{i+1} - t_i)(R_i + R_{i+1}), \quad (12)$$

where $i=0, 1, 2, \ldots$.

Similarly to equation (11), the next value of the indicator $A^*$ after a new test k+1, $A^*_{k+1}$ is given by equation (13) as follows:

$$A^*_{k+1} = \frac{\sum_{i=0}^{k} S_i}{(t_{k+1} - t_0)}.$$  (13)

Subtracting equation (11) from equation (13) gives equation (14):

$$(t_{k+1}-t_0)A^*_{k+1}=(t_k-t_0)A^*_k+S_k$$  (14), where $S_k$ is defined by equation (15) as follows:

$$S_k = \frac{1}{2}(t_{k+1} - t_k)(R_k + R_{k+1}).$$  (15)

Equations (14) and (15) combined together give the recursive relation defined by equation (16) as follows:

$$A^*_{k+1} = \frac{t_k - t_0}{t_{k+1} - t_0} A^*_k + \frac{(t_{k+1} - t_k)(R_k + R_{k+1})}{2(t_{k+1} - t_0)},$$  (16)

where k=1, 2, ..., n. Initial values for $A^*$ and $t_1$ are defined by equation (17), which allows the iterative computation of the Time Average Glucose indicator, and are as follows:

$$A^*_1 = R_0$$

$$t_1 = t_0$$  (17), where $R_0$ is an initial blood glucose test result, and $t_0$ is the time of the initial blood glucose test recorded, for example, by a blood glucose meter. It is to be appreciated that the software according to the present invention permits the user (e.g., under HCP instruction) to re-initialize (e.g., reset) the counter k to zero, whereby the next blood glucose test result then becomes the initial value $A_1^*$ from which a new Time Average Glucose is obtained over time via equation (16).

Figure 8:
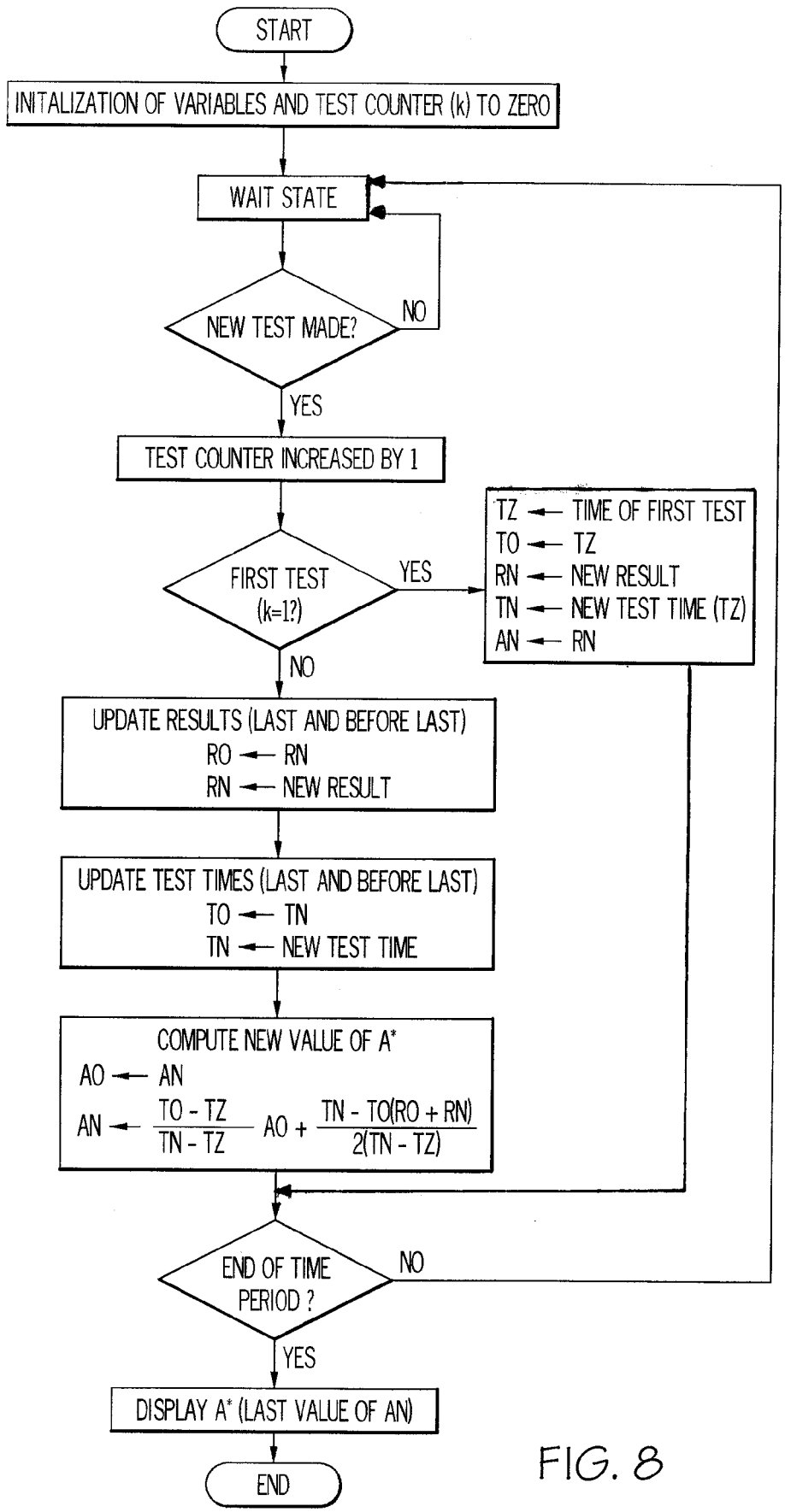
FIG. 8 is a flowchart of a method to compute an average of the approximated function $\Psi(t)$ according to an embodiment of the present invention.

To obtain the Time Average Glucose using equation (16), exactly 4 subtractions, 2 additions, 3 multiplications, and 2 divisions must be performed with each new test. FIG. 8 is a flowchart utilized for the computation of the average of the approximated function $\Psi(t)$. This flowchart is designed specifically to allow for implementation on a device with limited processing power and memory. The flow chart of FIG. 8 shows that the method implementation of the recursive relation of equation 16 starting with the initial values of equation 17 at a low processing cost.

The following variables are used in the flow chart of FIG. 8 with, between parentheses, the corresponding name used in the above equations: TZ is time of the first initial test ($t_0$), RN is a new result ($R_{k+1}$), RO is the previous result ($R_k$), TN is the time of the new result ($t_{k+1}$), TO is the time of the previous result ($t_k$), AN is the Time Average Glucose new value ($A_{k+1}^*$), and AO is the Time Average Glucose previous value ($A_k^*$). FIG. 9 shows in tabular form an example of the computation of Time Average Glucose ($A_k^*$) step by step as well as computation of the indicator VA1c, which discussed hereafter.

Method to Compute Indicator #2—Virtual Hemoglobin A1c

Since a linear relation between weighted average $C^*$ and VA1c is noted, $C^*$ is computed by equation (6) disclosed above previously. In some embodiments which may implement and use some or all the processes according to the present invention, because of response time constraints and the impracticality of the computation of the γ coefficients at each step, two different implementations for the evaluation of the weighted average $C^*$ were developed. In a first embodiment, for an implementation of equation (6) on a low processing power device (like a traditional blood glucose meter), pre-computed γ values are stored in a table and the iterative approach according to the present invention for computing the weighted average $C^*$ is used. The table in one embodiment provides 90 values, 1 per day for 90 days, and in other embodiments, may store more or less such γ values. In such an embodiment, at each step of the computation the table is consulted to determine the 2 values of the corresponding $\gamma_j$ and $\gamma_{j+1}$ coefficients. In another embodiment, such as implemented on a traditional computer, the previous iterative method is skip and all the parts of equation (4), including the $\gamma_j$ and $\gamma_{j+1}$ coefficients using the exponential decay function mentioned earlier and shown by FIG. 7, is computed directly.

Next, the method to compute the VA1c indicator proceeds exactly as it did for Indicator #1, the Time Averaged Glucose. A weighted area $U_i$, called a "cell", is defined by the weighted tests $R_i$ and $R_{i+1}$, and is given by equation (18) as follows:

$$U_i = \frac{1}{2}(\gamma_{j,i} R_i + \gamma_{j,i+1} R_{i+1})(t_{i+1} - t_i).$$  (18)

Accordingly, calling the value $P_{k+1}$ the value of the weighted average $C^*$ after completion of test k+1 for example at time $t_{k+1}$, $P_{k+1}$ can be given by equation (19) as follows:

$$P_{k+1} = \frac{\sum_{i=0}^{k} U_i}{(t_{k+1} - t_0)}.$$  (19)

In a manner similarly described previously above, subtracting $P_k$ from $P_{k+1}$ gives the recursive relation between $P_k$ and $P_{k+1}$, thus allowing the iterative computation of the indicator VA1c. The recursive relation for the weighted average is defined by equation (20) as follows:

$$p_{k+1} = \frac{t_k - t_0}{t_{k+1} - t_0} P_k + \frac{(t_{k+1} - t_k)(\gamma_{j,k} R_k + \gamma_{j+1,k+1} R_{k+1})}{2(t_{k+1} - t_0)},$$  (20)

where k=1, 2, 3, ..., n. Initial values for $P_1$ and $t_1$ are defined by equation (21), which allows the iterative computation of the Indicator #2, and are as follows:

$$P_1 = R_0$$

$$t_1 = t_0$$  (21), where $R_0$ is an initial blood glucose test result and $t_0$ is the time of the initial blood glucose test recorded, for example, by a blood glucose meter. It is to be appreciated that the software according to the present invention permits the user (e.g., under HCP instruction) to re-initialize (e.g., reset) the counter k to zero, whereby the next blood glucose test result then becomes the initial value $P_0$ from which a new weighted average C* is obtained over time via equation (20).

The "computing cost" per step for calculating C* using equation (20) is 4 subtractions, 2 additions, 5 multiplications, and 2 divisions after each new test (not including the table consultation required for the determination of the γ coefficients). Some of these calculations can be combined with those required for the computation of A* (indicator #1). From each value of P, the method applies the already defined relation of equation (7) to compute VA1c at the additional cost of 1 addition and 1 division, where the value 82/33 is a constant, and VA1c is computed according to equation (22) defined as follows:

$$VA1c = \frac{C^*}{33} + \frac{82}{33}. \tag{22}$$

Figure 10:
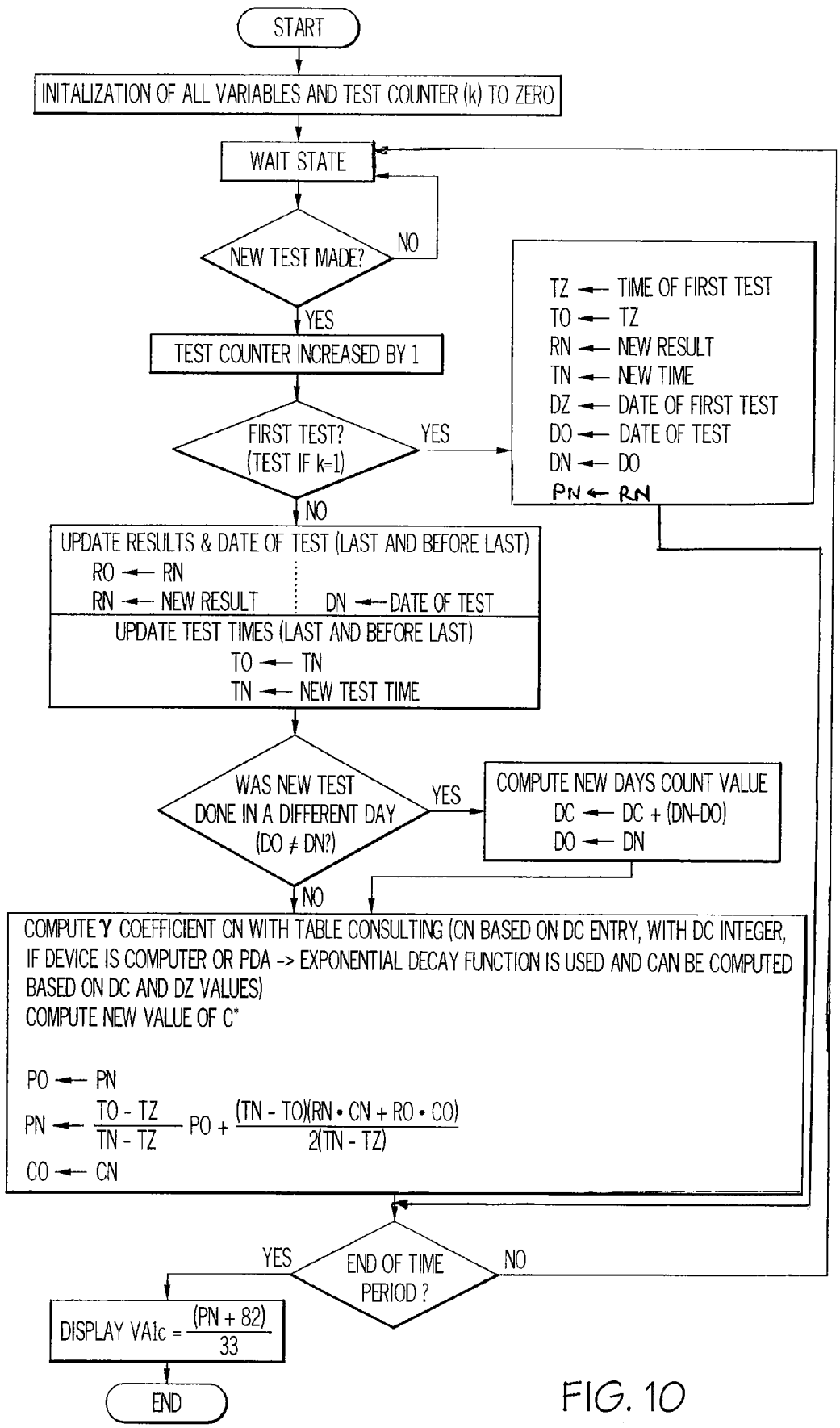
FIG. 10 is a flowchart of a method to compute VA1c according to an embodiment of the present invention.

FIG. 10 shows a detailed flow chart for the low implementation of the recursive relation of equation (20) with the initial condition of equation (21) and the calculation of VA1c using equation (22). The following variables are used in the flow chart: TZ is the time of the first test ($t_0$), RN is new result ($R_{k+1}$), RO is the previous result ($R_k$), TN is the time of new result ($t_{k+1}$), TO is the time of previous result ($t_k$), DZ is date of first test (start of the evaluation period), DN is the date of new test, DO is date of the previous test, DC is a day counter which counts days since the first test, CN is γ coefficient for new result ($\gamma_{j,k+1}$), CO is γ coefficient for the previous result ($\gamma_{j,k}$), PN is a new value of C* ($P_{k+1}$), and PO is the previous value of C* ($P_k$).

Method to Compute Indicator #3—Lability Factor

Indicator #3, the Lability Factor, is defined as the ratio of the standard deviation to the mean value $\mu_n$ of the tests during the time period considered expressed as a percentage. In order to establish a recursive relation, the variance of the test results is used, which is the square of the standard deviation and which is given by equation (23) as follows:

$$V_n = \frac{1}{n} \sum_{i=0}^{n} (R_i - \mu_n)^2, \tag{23}$$

where $R_i$ is test result #i and $\mu_n$ is the average of the test results $R_0$ to $R_n$. The mean value $\mu_n$ is given by equation (24) as follows:

$$\mu_n = \frac{1}{n+1} \sum_{i=0}^{n} R_i. \tag{24}$$

Expanding equation (23), the following equation (25) is obtained:

$$nV_n = \sum_{i=0}^{n} R_i^2 - 2\mu_n \sum_{i=0}^{n} R_i + (n+1)\mu_n^2, \tag{25}$$

which can be re-written by substituting in equation (24) as either equation (26) or equation (27) as follows:

$$nV_n = \sum_{i=0}^{n} R_i^2 - \frac{1}{n+1}\left(\sum_{i=0}^{n} R_i\right)^2, \tag{26}$$

or $$(n-1)V_{n-1} = \sum_{i=0}^{n-1} R_i^2 - \frac{1}{n}\left(\sum_{i=0}^{n-1} R_i\right)^2. \tag{27}$$

From the mean value relation $$\mu_n = \frac{1}{n+1} \sum_{i=0}^{n} R_i,$$

equation (28) is also obtained as follows:

$$\mu_n = \frac{n}{n+1}\mu_{n-1} + \frac{R_n}{n+1}, \tag{28}$$

with the initial values $\mu_0 = R_0$, and $$\mu_1 = \frac{R_0 + R_1}{2}.$$

In order to get the recursive relation for the variance, equation (27) is subtracted from equation (26), and using equation (28) the following recursive relation equation (29) is obtain:

$$V_n = \frac{n-1}{n}V_{n-1} + \frac{1}{n}R_n^2 - \frac{n+1}{n}\mu_n^2 + \mu_{n-1}^2, \tag{29}$$

where n=2, 3, 4, . . . and with the initial condition values $V_0$=0 and $$V_1 = \frac{1}{2}(R_1 - R_0)^2.$$

Figure 11:
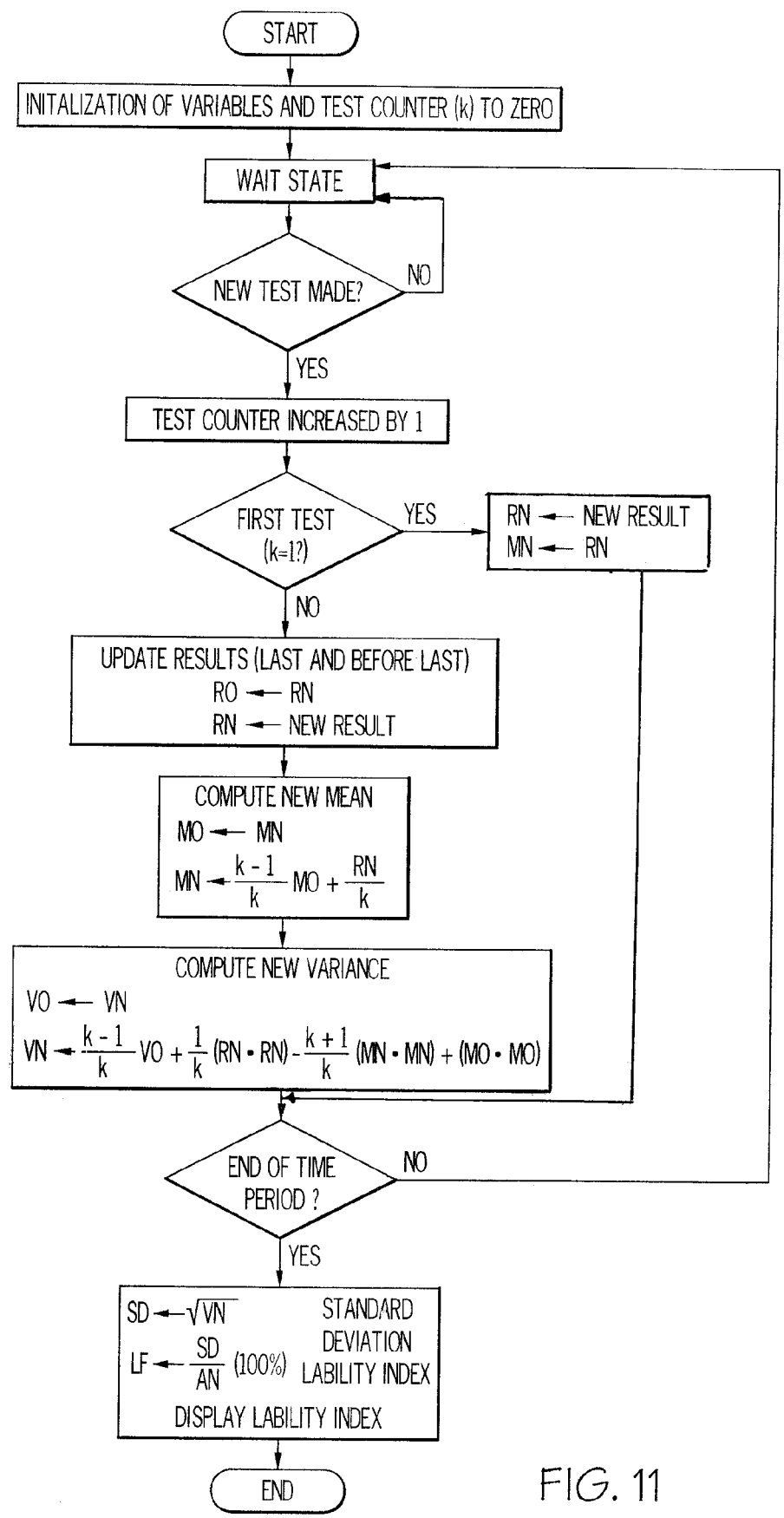
FIG. 11 is a flowchart of a method to compute a Lability Factor with recursive relations according to an embodiment of the present invention.

The recursive relation according to equation (29), along with the initial conditions values, allows the step by step computation of the variance. Once the variance is calculated, the standard deviation (square root of the variance) is calculated, and then the Lability factor is expressed as a percentage of the ratio of the standard deviation to the Time Averaged Glucose value A*. Therefore, it is to be appreciated that the computation of the Time Averaged Glucose and the Lability Factor are provided at the cost per step of 6 subtractions, 5 additions, 10 multiplications, 6 divisions, and a square root. FIG. 11 shows a detailed flow chart for the low implementation of the recursive relation, equation (29), with the initial condition $V_0$=0 and $$V_1 = \frac{1}{2}(R_1 - R_0)^2,$$

the calculation of the Lability Factor. The following variables are used in the flow chart: RN is the New Result ($R_{k+1}$), RO is the previous result ($R_k$), MN is the New Mean value of the tests ($\mu_k$), MO is the previous mean value of the tests (#$\mu_{k-1}$), VN is the new value of Variance ($V_{k+1}$), VO is the previous value of Variance ($V_k$), SD is the standard deviation, and LF is the Lability Factor. FIG. 12 is a table showing the results of the iterative computation of the variance, the standard deviation, and the Lability Factor.

All these new blood glucose functions can be computed by a microprocessor in any blood glucose meter or by download of blood glucose time stamped values into a free standing computer. This time encoded blood glucose information is already available in all commercial blood glucose monitoring devices. All parameters are tabulated in a recursive manner based on a simple update calculation which occurs each time a new test is performed, thereby allowing implementation in most current blood glucose meters without the requirement of additional processing power (as opposed to a complete re-calculation with every new test).

In one embodiment, the methods according to the present invention is provided as interactive implementation on a general purpose computer where the patient or a professional has downloaded the time stamped test results from a blood glucose meter and then interactively selected one of several time periods to assess the patient's overall glycemic control. Thus, this invention immediately allows patients, physicians and health plan managers to access a simple summary of how tightly blood glucose has been controlled over the last few months and to assess the variability of glucose control over the same time frame without undertaking any additional blood drawing or testing.

While the present invention has been described in particular embodiments, the present invention should not be construed as limited by such embodiments, but rather, according to the claims below.

What is claimed is:

1. A method for determining a stability of a blood glucose concentration of a patient, the method comprising:
   receiving, at a processor, a plurality of blood glucose concentration test results each taken from the patient at a different time over a time period;
   approximating, by the processor, a plurality of blood glucose concentration test result values as functions of time from consecutive samples of the plurality of blood glucose concentration test results;
   computing, by the processor, a time averaged glucose value as a first indicator by averaging the approximated blood glucose concentration test result values over the time period such that the first indicator is an indication of a blood glucose control normalized for each time interval between the consecutive samples;
   applying, by the processor, a time-based weight to each of the blood glucose concentration test results by multiplying each of the blood glucose concentration test results by a respective coefficient, wherein the weights are time-based such that each successive coefficient is less than each previous coefficient as a function of increasing time;
   computing, by the processor, a weighted average by averaging the time-based weighted blood glucose concentration test results;
   computing, by the processor, a simulated measurement of a blood hemoglobin as a second indicator by correlating with a pre-determined formula the weighted average of the time-based weighted blood glucose concentration test results and the blood hemoglobin;
   computing, by the processor, a variance of the blood glucose concentration test results;
   computing, by the processor, a standard deviation from of the variance of the blood glucose concentration test results;
   computing, by the processor, a ratio of the standard deviation to the time averaged glucose value to give a third indicator representing variability of blood glucose concentration over the time period; and
   providing, by the processor, the first, second, and third indicators to a user interface or display.

2. The method of claim 1, wherein at least one of the averaging and computing the variance steps is performed in a recursive manner.

3. The method of claim 1, wherein the approximating is accomplished using the trapezoidal rule.

4. The method of claim 1 wherein the pre-determined formula correlating the average of time-based weighted blood glucose concentration test results and the blood hemoglobin is a linear regression formula.

5. The method of claim 1, wherein the blood hemoglobin is A1c.

6. The method of claim 1, further comprises representing the ratio as a percentage.

7. A system for determining a stability of a blood glucose concentration of a patient, the system comprising:
   a processor programmed to:
   receive a plurality of blood glucose concentration test results each taken from the patient at a different time over a time period;
   compute a time-averaged glucose parameter through an averaging of approximated blood glucose concentration test result values as functions of time, such that in this average, each successive result value in time is weighted less than each previous result value in time as a function of increasing time, wherein the time-averaged glucose parameter is indicative of a blood glucose concentration control normalized for each time interval between the consecutive samples over the time period;
   compute a virtual blood hemoglobin parameter through a simulated measurement of a blood hemoglobin through a pre-determined formula correlating an average of time-based weighted blood glucose concentration test results and the blood hemoglobin, the virtual blood hemoglobin parameter being indicative of blood glucose concentration control over an extended time period encompassing the time period;
   compute a lability factor parameter through a ratio of a standard deviation calculated from a variance of the blood glucose concentration test results to the approximated blood glucose concentration test result values average, the lability factor parameter being indicative of a variability in blood glucose concentration over the time period; and
   provide the time-averaged glucose parameter, the virtual blood hemoglobin parameter, and the lability factor parameter to a user interface or display.

8. The system of claim 7, wherein the processor is programmed to compute at least one of the time-averaged glucose parameter, the virtual blood hemoglobin parameter, and the lability factor parameter in a recursive manner.

9. The system of claim 7, wherein the time-averaged glucose parameter is computed by the processor by being programmed to:
   use a rule to approximate a plurality of blood glucose concentration test result values as functions of time from consecutive ones of the plurality of blood glucose concentration test results; and average the approximated blood glucose concentration test result values over the time period.

10. The system of claim 9, wherein rule is a Newton-Cotes formula rule.

11. The system of claim 9, wherein rule is the trapezoidal rule.

12. The system of claim 9, wherein the lability factor parameter is computed by the processor:
    computing a variance of the blood glucose concentration test results;
    computing a standard deviation of the variance of the blood glucose concentration test results; and
    computing the ratio of the standard deviation to the time-averaged glucose parameter.

13. The system of claim 7, wherein the virtual blood hemoglobin parameter is computed by the processor being programmed to:
    apply a time-based weight to each of the blood glucose concentration test results by multiplying each of the blood glucose concentration test results by a respective coefficient;
    compute a weighted average by averaging the time-based weighted blood glucose concentration test results; and
    correlating the weighted average of the time-based weighted blood glucose concentration test results and the blood hemoglobin with a pre-determined formula.

14. The system of claim 7, wherein the system is provided to a blood glucose meter.

15. The system of claim 7, wherein the system is provided to a computer.

16. The system of claim 7, wherein the processor is programmed to receive the plurality of glucose measurements from memory.

17. The system of claim 16, wherein the memory is external to the system.

18. A non-transitory computer-usable medium providing computer readable instructions for execution by a processor to perform a method comprising:
    approximating a plurality of blood glucose concentration test result values as functions of time from consecutive samples of a plurality of blood glucose concentration test results;
    computing a time averaged glucose value as a first indicator by averaging the approximated blood glucose concentration test result values over the time period such that the first indicator is an indication of a blood glucose control normalized for each time interval between the consecutive samples;
    applying a time-based weight to each of the blood glucose concentration test results by multiplying each of the blood glucose concentration test results by a respective coefficient, wherein the weights are time-based such that each successive coefficient is less than each previous coefficient as a function of increasing time;
    computing a weighted average by averaging the time-based weighted blood glucose concentration test results;
    computing a simulated measurement of a blood hemoglobin as a second indicator by correlating with a pre-determined formula the weighted average of the time-based weighted blood glucose concentration test results and the blood hemoglobin;
    computing a variance of the blood glucose concentration test results;
    computing a standard deviation from of the variance of the blood glucose concentration test results;
    computing a ratio of the standard deviation to the time averaged glucose value to give a third indicator representing variability of blood glucose concentration over the time period; and providing the first, second, and third indicators to a user interface or display.

* * * * *

UNITED STATES PATENT AND TRADEMARK OFFICE
CERTIFICATE OF CORRECTION

| | | |
|---|---|---|
| PATENT NO. | : 8,117,020 B2 | |
| APPLICATION NO. | : 12/437933 | |
| DATED | : February 14, 2012 | |
| INVENTOR(S) | : Daniel S. Abensour et al. | |

It is certified that error appears in the above-identified patent and that said Letters Patent is hereby corrected as shown below:

Col. 1, Line 19, "and in particularly" should read --and in particular--

Col. 1, Line 38, "office, making, availability" should read --office, making availability--

Col. 1, Line 51, "Typically a" should read --Typically, a--

Col. 4, Line 57, "representations shows" should read --representation showing--

Col. 4, Line 62, "invention" should read --invention.--

Col. 4, Line 66, "step by step" should read --step-by-step--

Col. 5, Line 6, "showing result" should read --showing results--

Col. 5, Line 39, "that can functions" should read --that can function--

Col. 6, Lines 15-16, "Likewise such computer instructions may be provides" should read --Likewise, such computer instructions may be provided--

Col. 6, Line 43, "is a docket" should read --is a docking--

Col. 6, Line 45, "may provided" should read --may provide--

Col. 7, Lines 16-17, "may include, but not limited thereto" should read --may include, but is not limited thereto--

Col. 7, Line 30, "such as for example," should read --such as, for example,--

Col. 8, Line 9, ",such the" should read --,such as the--

Signed and Sealed this
Twenty-eighth Day of August, 2012

David J. Kappos
*Director of the United States Patent and Trademark Office*

Col. 8, Line 12, "include but not limited" should read --include, but are not limited--

Col. 8, Line 30, "to generated reports" should read --to generate reports--

Col. 8, Line 39, "description etc." should read --description, etc.--

Col. 8, Line 41, "description etc." should read --description, etc.--

Col. 8, Line 55, "a health care provided" should read --health care provided--

Col. 8, Line 58, "invention is" should read --invention are--

Col. 9, Line 13, "Time Averaged Glucose-over" should read --Time-Averaged Glucose over--

Col. 9, Line 21, "Time Averaged Glucose" should read --Time-Averaged Glucose--

Col. 9, Line 34, "patients' blood" should read --patient's blood--

Col. 9, Line 41, "Time Averaged Glucose" should read --Time-Averaged Glucose--

Col. 9, Line 49, "Time Averaged Glucose" should read --Time-Averaged Glucose--

Col. 9, Line 55, "Time Averaged Glucose" should read --Time-Averaged Glucose--

Col. 9, Line 56, "Time Averaged Glucose" should read --Time-Averaged Glucose--

Col. 9, Lines 58-59, "Time Averaged Glucose" should read --Time-Averaged Glucose--

Col. 10, Line 20, "prior and c)" should read --prior, and c)--

Col. 10, Line 24, "are may be" should read --may be--

Col. 10, Line 31, "electophoretically" should read --electrophoretically--

Col. 10, Line 39, "the control-of blood" should read --the control of blood--

Col. 10, Line 42, "Time Averaged Glucose" should read --Time-Averaged Glucose--

Col. 11, Line 16, "value this is defined" should read --value that is defined--

Col. 11, Line 36, "Time Averaged Glucose" should read --Time-Averaged Glucose--

Col. 11, Line 43, "is a desired" should read --is desired--

CERTIFICATE OF CORRECTION (continued)
U.S. Pat. No. 8,117,020 B2

Col. 11, Line 44, "embodiments other rules" should read --embodiments, other rules--

Col. 12, Line 22, "by a health care provided" should read --by health care provided--

Col. 12, Line 49, "For the aforementioned simulation it" should read --For the aforementioned simulation, it Col. 12, Line 51, "For example if the" should read --For example, if the--

Col. 14, Line 25, "meter, pda" should read --meter, PDA--

Col. 14, Line 41, "Time Averaged Glucose" should read --Time-Averaged Glucose--

Col. 15, Line 32, "Time Averaged Glucose" should read --Time-Averaged Glucose--

Col. 15, Line 44, "Time Averaged Glucose" should read --Time-Averaged Glucose--

Col. 15, Line 46, "Time Averaged Glucose" should read --Time-Averaged Glucose--

Col. 15, Line 52, "The flow chart" should read --The flowchart--

Col. 15, Line 55, "equation 16 starting with" should read --equation 16 starts with--

Col. 15, Line 57, "flow chart" should read --flowchart--

Col. 15, Line 62, "Time Averaged Glucose" should read --Time-Averaged Glucose--

Col. 15, Line 63, "Time Averaged Glucose" should read --Time-Averaged Glucose--

Col. 15, Line 65, "Time Averaged Glucose" should read --Time-Averaged Glucose--

Col. 15, Line 66, "which discussed hereafter" should read --which is discussed hereafter--

Col. 16, Line 22, "method is skip" should read --method is skipped--

Col. 16, Line 26, "Time Averaged Glucose" should read --Time-Averaged Glucose--

Col. 17, Line 20, "flow chart" should read --flowchart--

Col. 17, Lines 24-25, "flow chart" should read --flowchart--

Col. 17, Line 25, "RN is new result" should read --RN is the new result--

Col. 17, Line 27, "DZ is date" should read --DZ is the date--

CERTIFICATE OF CORRECTION (continued)
U.S. Pat. No. 8,117,020 B2

Col. 17, Lines 28-29, "date of new test. DO is date of" should read
--date of the new test, DO is the date of--

Col. 17, Line 30, "for new result" should read --for the new result--

Col. 18, Line 33, "is obtain" should read --is obtained--

Col. 18, Line 51, "Lability factor" should read --Lability Factor--

Col. 18, Line 52, "Time Averaged Glucose" should read --Time-Averaged Glucose--

Col. 18, Line 54, "Time Averaged Glucose" should read --Time-Averaged Glucose--

Col. 18, Line 57, "flow chart" should read --flowchart--

Col. 18, Line 66, "flow chart" should read --flowchart--

Col. 20, Line 1, "from of the variance" should read --from the variance--